(12) United States Patent
Regnier

(10) Patent No.: US 11,389,657 B2
(45) Date of Patent: Jul. 19, 2022

(54) AUTONOMOUS IMPLANTABLE CAPSULE FOR HEART STIMULATION

(71) Applicant: SORIN CRM SAS, Clamart (FR)

(72) Inventor: Willy Regnier, Longjumeau (FR)

(73) Assignee: Sorin CRM SAS, Clamart (FR)

( * ) Notice: Subject to any disclaimer, the term of this patent is extended or adjusted under 35 U.S.C. 154(b) by 821 days.

(21) Appl. No.: 15/479,095

(22) Filed: Apr. 4, 2017

(65) Prior Publication Data
US 2018/0185638 A1 Jul. 5, 2018

(30) Foreign Application Priority Data

Dec. 30, 2016 (EP) ...................................... 16306851
Dec. 30, 2016 (EP) ...................................... 16306852
Dec. 30, 2016 (EP) ...................................... 16306853

(51) Int. Cl.
| A61N 1/362 | (2006.01) |
|---|---|
| H02N 2/18 | (2006.01) |
| A61N 1/365 | (2006.01) |
| H01L 41/113 | (2006.01) |

(Continued)

(52) U.S. Cl.
CPC ......... *A61N 1/362* (2013.01); *A61N 1/36542* (2013.01); *A61N 1/3756* (2013.01); *A61N 1/3785* (2013.01); *H01L 41/1136* (2013.01); *H02N 2/18* (2013.01)

(58) Field of Classification Search
CPC .............. A61N 1/3756; A61N 1/37205; A61N 1/0558; A61N 1/37518; A61N 1/3956; A61N 1/362; A61N 1/057; A61N 1/36125; A61N 1/375; A61N 1/05; A61N 1/36; A61N 1/3752; A61N 1/3758; A61N 1/3968; A61B 5/0031; A61B 5/4836; A61B 5/686; A61B 5/4848; A61B 5/486; A61B 5/6861; A61B 5/6882; A61B 2562/16; A61B 2562/162; A61B 2562/227; A61B 2576/02; A61B 5/6869
See application file for complete search history.

(56) References Cited

U.S. PATENT DOCUMENTS

| 3,943,936 A | 3/1976 | Rasor et al. |
|---|---|---|
| 5,885,471 A | 3/1999 | Ruben et al. |

(Continued)

FOREIGN PATENT DOCUMENTS

| EP | 2 520 333 A1 | 11/2012 |
|---|---|---|
| EP | 2 638 930 A1 | 9/2013 |
| EP | 2 639 845 A1 | 9/2013 |

(Continued)

OTHER PUBLICATIONS

International Search Report and Written Opinion on PCT application PCT/EP2017/084617 dated Jun. 7, 2018. 9 pages.

*Primary Examiner* — Deborah L Malamud
(74) *Attorney, Agent, or Firm* — Foley & Lardner LLP

(57) ABSTRACT

The implant including an elongated tubular body, having at a first end a releasable device connected to an installation lead, and at a second end a member for anchoring to a heart wall, the tubular body housing a frame supporting an electronic unit. The implant further comprises an accelerometer. This accelerometer comprises a piezoelectric blade extending in cantilever from an embedding section of the frame, in a direction going from the first end to the second end.

20 Claims, 12 Drawing Sheets

(51) Int. Cl.
*A61N 1/375* (2006.01)
*A61N 1/378* (2006.01)

(56) References Cited

U.S. PATENT DOCUMENTS 8,644,934 B2 * 2/2014 Hastings ............ A61N 1/37512
607/32
2007/0293904 A1 * 12/2007 Gelbart ................ A61N 1/3785
607/35

FOREIGN PATENT DOCUMENTS

| EP | 2 857 064 A1 | 4/2015 |
| EP | 2 857 065 A1 | 4/2015 |
| EP | 2 959 940 A1 | 12/2015 |
| WO | WO-2007/149462 A2 | 12/2007 |

* cited by examiner

AUTONOMOUS IMPLANTABLE CAPSULE FOR HEART STIMULATION

CROSS-REFERENCE TO RELATED PATENT APPLICATIONS

This application claims priority to and the benefit of European Patent Application Number 16306851.3, filed Dec. 30, 2016, European Patent Application Number 16306852.1, filed Dec. 30, 2016, and European Patent Application Number 16306853.9, filed Dec. 30, 2016, all of which are hereby incorporated by reference in their entireties.

FIELD OF TECHNOLOGY

The disclosure relates to "active implantable medical devices" as defined by directive 90/385/CEE of 20 Jun. 1990 of the Council of the European Communities, more specifically implants that allow continuous heart rate monitoring and deliver, if necessary, electrical pulses for stimulation, resynchronization and/or defibrillation to the heart, in case of rhythm disruption detected by the device.

The disclosure relates, more specifically, an implant used in cardiac rhythm management to generate electrical energy and more specifically, a miniaturized leadless endocavitary stimulation device.

BACKGROUND

Recent advances in the fields of active equipment miniaturization and life sciences have paved the way for the development of a large variety of miniaturized implantable systems to be used for monitoring, diagnosis or treatment. Progress on this front has led to a surge in demand for these miniaturized systems—both from doctors and patients—as they provide less invasive implantation procedures, more comfort, improved performances, and often lead to new diagnoses and treatment types.

In the case of active cardiac stimulation-type implants, while voluminous, traditional implants are placed remotely and must be linked to the stimulation site by a lead, miniaturization has led to the development of systems that are so small in size that they can be completely implanted on site, for example, directly into a heart cavity, while functioning autonomously. These implants are referred to as without lead or leadless implants. These systems can be endocardial, if placed inside one of the heart cavities, or epicardial, if fixed to the outer wall of the myocardium.

The leadless endocardial stimulation-type implants possess a cylindrical, capsule-like shape enabling them to be inserted longitudinally, using a catheter-type system going through the venous or arterial system. A fastening device is located at the end of the cylinder in order to attach the implant at the desired location for stimulation.

Leadless implants are made of a single hollow body, which contains the electronic-type elements, power source, communication module, and which has clamping and connection adjustments with the delivery system externally.

In order to mechanically measure the cardiac activity and manage the stimulation accordingly, it is common to equip an implant with an accelerometer. The latter is generally made up of a specific component welded to the implant's electronic card and occupies a certain amount of space on this card. U.S. Pat. No. 5,885,471 A describes such an accelerometer.

For the leadless implants currently available on the market, the operating lifetime is about 8 to 10 years, depending on the device's utilization rate, and is directly related to the battery's lifespan. Lithium Carbon Monofluoride (Li-CFx) technology is used for this type of battery, mostly for its long life cycle and low discharge rate.

Piezoelectricity is a possible energy-generating alternative, which is used in the field of MEMS sensors as well as actuators. The use of piezoelectricity to produce electrical energy in an implant is already known.

The EP 2639845 A1, EP 2638930 A1, EP 2857064 A1, EP 2857065 A1 and EP 2520333 A1 patent applications describe a number of techniques enabling to generate energy in a leadless capsule, in particular on the basis of moving masses and piezoelectricity.

The present disclosure aims to enable a capsule-type implant of the abovementioned type, which can integrate a piezoelectric generator element with moving mass, meeting the dimensional requirements for this type of application and allowing improving energy recovery.

In particular, the disclosure aims to integrate such a generator element by improving the available space in order to maintain an appropriate size without sacrificing other industrial requirements for this type of product, by implementing compact, reliable and easy-to-industrialize means for mounting an electrical energy generator of the piezoelectric-type without moving mass.

The aim of the disclosure is, for a previously mentioned-type implant, to reduce the space required for the accelerometer, whilst receiving acceleration signals in an improved way. Another aim of the present disclosure, in one of its embodiments, is to integrate in a practical, reliable and efficient way the accelerometer and energy-recovering features into such an implant, while ensuring the latter retains an appropriate size without having to sacrifice industrial requirements which apply to this type of product.

SUMMARY

For this purpose, the disclosure proposes an implant. The implant, such as an autonomous heart stimulation capsule, includes an elongated tubular body, at one end of the body, an anchoring element of the implant to a heart wall. The tubular body has a frame supporting an electronic unit and a generator of electrical energy.

One embodiment relates to disclose an implant, such as a heart implant, in particular an autonomous heart stimulation capsule, including an elongated tubular body possessing, at a first end, a releasable linking device connectable to an installation lead, and at a second end, an anchoring element for anchoring the implant to a heart wall, the tubular body housing a frame supporting an electronic unit and an accelerometer.

According to various embodiments, the accelerometer comprises a piezoelectric blade extending cantilevered from an end region of the piezoelectric blade embedded into the frame and in a direction from the first end to the second end.

Indeed, in contrast to what the skilled person would think, it has been observed that signals of piezoelectric origin, in particular accelerometric signals, were of a higher level and less subject to interference when the blade extended in cantilever from a remote region of the anchorage area to the heart wall and towards this anchoring region than in the opposite case.

According to various additional embodiments:
the piezoelectric blade also forms an electrical energy generator to supply the electronic unit;

the implant includes an inertial mass attached to the piezoelectric blade in an area away from the embedding region;

this inertial mass has dimensions which decrease when moving away from the piezoelectric blade's embedding region;

this inertial mass includes two identical elements attached one on each side of the blade, in particular in a free end region of the blade;

the piezoelectric blade includes on each one of its sides a first metallization for collecting an acceleration signal and a second metallization for collecting electrical energy, at least a part of the implant's electrical supply voltage;

the metallizations each include a capture area located in the end region of the blade, opposite to the embedding region of the piezoelectric blade;

the first metallization includes an area extending along the edge of the blade, between the capture area and the embedding region of the piezoelectric blade;

the frame includes two frame elements that are assembled to each other, in some embodiments in a radially direction, the piezoelectric blade's embedding region being clamped between two opposing sections, in particular end sections, of the two frame elements of the frame;

the implant includes, at the level of said opposing sections a clamping ring holding said opposing sections of the two frame elements of the frame;

the piezoelectric blade's embedding region is located in the vicinity of the first implant's end;

the implant includes a second piezoelectric blade functioning as generator for collecting electrical energy, in particular at least a part of the implant's electrical supply voltage, in particular to supply the electronic unit;

the first and second piezoelectric blades are embedded in the same section of the frame and in some embodiments extend in cantilever essentially parallel to one another and in some embodiments, the blades extend in the same direction from said frame section.

the first piezoelectric blade is smaller than the second piezoelectric blade.

In another embodiment, the frame comprises discrete regions, the electrical energy generator includes a piezoelectric blade having an attachment region, a free intermediate region and a region to which is attached an inertial mass, the generator extends in a cantilevered way from the attachment region, the latter being secured to one of the support regions, and the electronic unit is located at said free intermediate region of the piezoelectric blade.

According to various additional embodiments:

the electronic unit includes two elements arranged one on each side of the blade's free intermediate region, in some embodiments the two elements are electrically connected by a flexible conductive sheet;

the support regions are connected together by longitudinal arms, in some embodiments the arms have adjustments for the reception of the electronic unit;

the frame includes a specific element for receiving the electronic unit;

the frame is made up of two elements radially assembled to one another, in some embodiments the piezoelectric blade's attachment region sandwiched between two sides opposite the two elements of the frame by a clamping ring of the two elements of the frame at the level of said opposing sides;

the implant includes an anchoring element to allow implantation to a heart wall, and the piezoelectric blade's attachment region is located in the implant's end region, opposite to the anchoring element;

the inertial mass has dimensions which decrease when moving away from the blade's attachment region;

the inertial mass includes two generally identical elements located one on each side of the blade in a free end region of the latter, in some embodiments with a direct adhesive bond between the two elements of the inertial mass in the vicinity of the blade's free end region.

In various embodiments: the generator of electrical energy includes a piezoelectric blade having an attachment region, said piezoelectric blade being embedded in the frame at the attachment region, a free intermediate region and a region to which is attached an inertial mass, the generator extends in a cantilever way from the blade's attachment region, and the attachment region is located in the vicinity of the end of the implant opposite to the anchoring element.

According to various additional embodiments:

the blade's attachment region is embedded in a first support section of the frame acting as a support against an inner side of the elongated tubular body, such as with a frame that includes a second support section separated from the first support section and joined together by longitudinal arms including clamps, for receiving the electronic unit;

the attachment region is arranged between two sections of the first support section of the frame displaceable with respect to each other, and there is a clamping piece that exerts a force on both sections of the first support section of the frame in order to bring them closer to each other;

these two sections of the first support section of the frame have a non-circular contour, and the clamping piece includes a generally circular, elastically deformable ring adapted to be engaged on said contour after elastic deformation, then released to apply said force to said sections;

the implant includes a second ring adapted to be engaged on two sections of the second support section of the frame defining the second support section;

the frame is made of two assembled components to one another, such as assembled in the radial direction;

the frame is formed by an overmolding;

a second overmolding is formed on the blade's attachment region, such as an overmolding embedded into a corresponding recess formed in a section of the frame;

the first overmolding is positioned on the second overmolding and on the electronic unit, the inertial mass has dimensions which decrease when moving away from the blade's attachment region;

the electronic unit includes two elements arranged one on each side of the blade's free intermediate region;

the frame includes at least one additional means for retaining the blade's attachment region, such as a cylindrical pin or a wall.

BRIEF DESCRIPTION OF THE DRAWINGS

Embodiments of the present disclosure will now be described in reference to the attached drawings, wherein identical references from one figure to the next, designate components which are either identical or functionally similar.

DETAILED DESCRIPTION

An energy recovery device made to supply an autonomous miniaturized active implant positioned in a heart cavity, with improved attaching means for a piezoelectric element will now be described.

Figure 1:
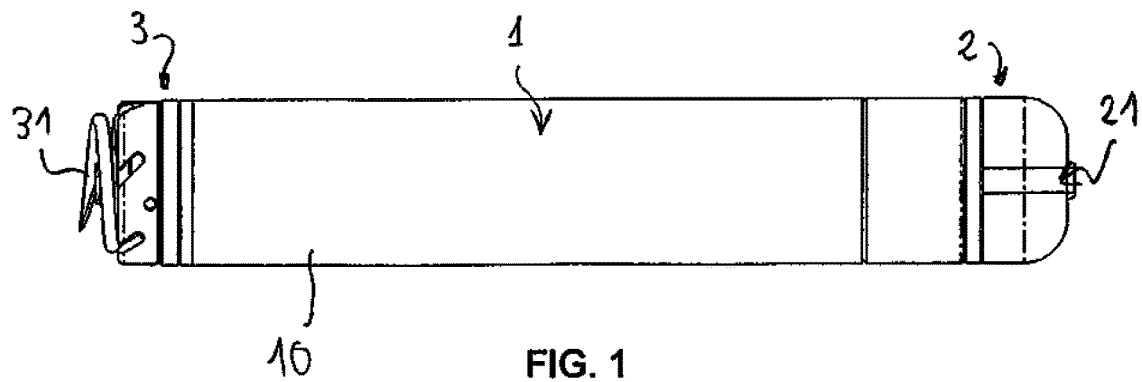
FIG. 1 is an overall view in side elevation of an implantable capsule, according to an exemplary embodiment.

FIG. 1, first of all, presents an autonomous capsule according to the disclosure. With the exception of the electrical energy-generating device, this capsule is related to the teachings of EP 2 959 940 A1 (Sorin CRM).

This capsule comprises a generally cylindrical body 1 formed mainly by a hollow tubular casing 10, of which a rear region 2 is fitted with a releasable linking device 21 with an installation lead, and of which a front region 3 has an anchor element 31 capable of perforating the endothelium upon rotation of the capsule and anchoring the latter to the heart wall. After this anchorage, the connection between the lead and the capsule is released and the lead is withdrawn.

Figure 2:
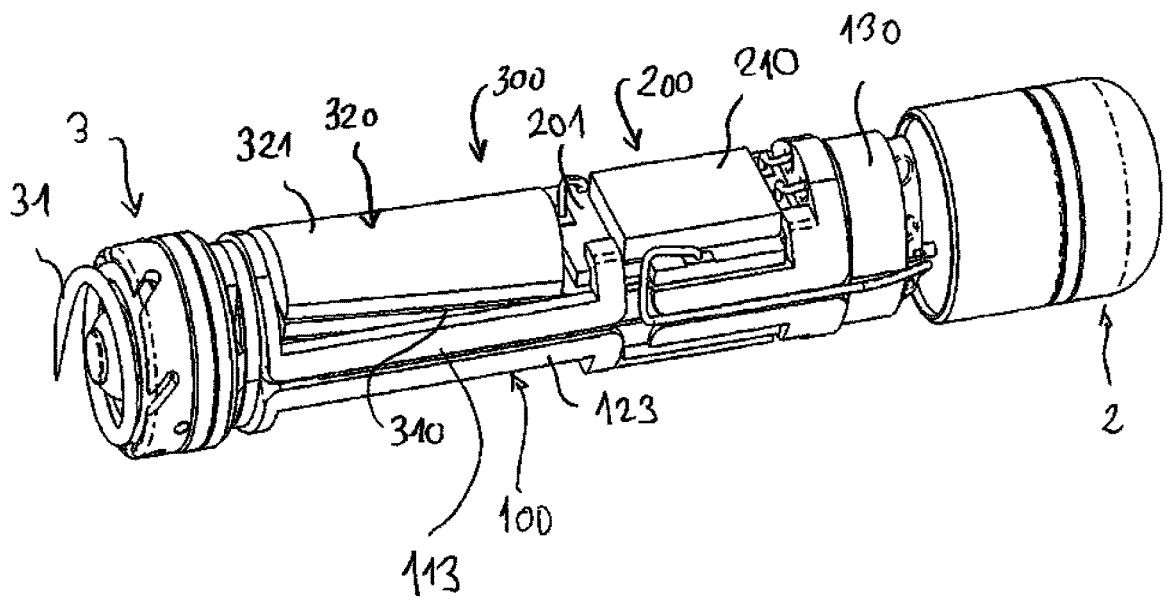
FIG. 2 is a perspective view of the capsule, its tubular casing being removed.

FIG. 2 shows the inner structure of the capsule, its external casing 10 being removed. The capsule comprises an inner frame 100 which receives the different functional components, mostly electronic circuits 200 used for heart monitoring and stimulation, and an energy generator 300.

The implant also comprises a battery whose charge is to be established and maintained by the energy generator 300. Due to the presence of the latter, the battery can be substantially smaller than in known implants of this type, while giving the implant a lifespan that is no longer dependent on the battery's capacity and the circuit's consumption.

Referring to FIGS. 3 to 12, the energy generator is composed of an elongated piezo-electrical blade 310, preferably of bimorph-type, that is to say capable of generating energy on both sides when it is subjected to a deformation, and an inertial mass 320. The blade 310 comprises a first end region 311 for its installation in the frame 100 of the implant, an intermediate free region 312 and a region 313 for attaching the inertial mass 320.

The latter has two components 321, 322 forming together a truncated cone, fixed one on each side of the blade 310 in a free region of the latter, for example by gluing. In its longitudinally opposite region 311, the blade 310 is fixed to the frame 100 by embedding, as we shall see below.

The blade 310 is subjected to a vibration deformation on both sides of a neutral or non-deformed position. The blade being held securely at its embedded end 311, its section extending cantilever from this end deforms itself with each heart beat and generates energy. The latter is recovered to recharge the abovementioned battery.

It is to be noted that the blade can extend itself throughout the interstitial space between the two elements 321, 322, or alternatively cover only a section of this space. In this case, and as illustrated, the space 325 that is not occupied with the blade is filled, for example, with glue. The presence of such a space enables to reduce the blade length and therefore its cost, and further reinforces the mechanical cohesion of the unit.

It is further noted that, particularly interesting, by placing the embedding region 311 of the blade at the implants end opposite to the implant's anchor element 31 that the energy recovery during movements related to the heartbeats is further improved.

In a non-illustrated variation, the blade 310 in its portion extending between the two elements 321, 322 is perforated with one or more through-holes, which is not shown in the figures, so that the glue used to bind the elements 321, 322 and the blade can provide a direct adhesion between the two elements.

The material used for the elements 321, 322 forming the inertial mass is in this example tungsten, a high density material which makes it possible to keep production costs under control.

In some embodiments, the weight of the components is adjusted to the blade's geometry and elastic properties in order to reach a desired resonance frequency and desired amplitude of movement, thereby improving the energy production.

The conicity of the outer surfaces of the mass elements 321, 322 allows an improvement in the use of the available space before entering in contact with the inside of the tube constituting the body of the implantable capsule. This conical geometry is not exhaustive and can be adapted to its environment in order to improve the mass/congestion ratio.

In this example, the dimensions of the blade are between 10 and 30 mm in length, 2 to 5 mm in width and less than 05 mm in thickness. The mass has dimensions adjusted to the final dimensions necessary for the desired vibration mode, for this example, the length is between 5 and 15 mm, the width is identical to that of the blade and the height is between 0.5 and 2 mm depending on the movement allowed by the implant's tubular geometry.

The internal mechanical architecture of the implant will now be described, and first of all, how the energy generator 300 is fixed to the frame 100.

The frame is made of two elongated elements 110, 120, generally symmetrical with respect to a longitudinal plane, each element having at each end a longitudinal end section, generally of a semi-elliptical shape 111, 121 and 112, 122 respectively as well as lateral arms, respectively 113, 123 and 114, 124, joining longitudinally these longitudinal end sections. In this embodiment, the two end sections 111, 121 form the first support section and the two end sections 112, 122 form the second support section.

Figure 3:
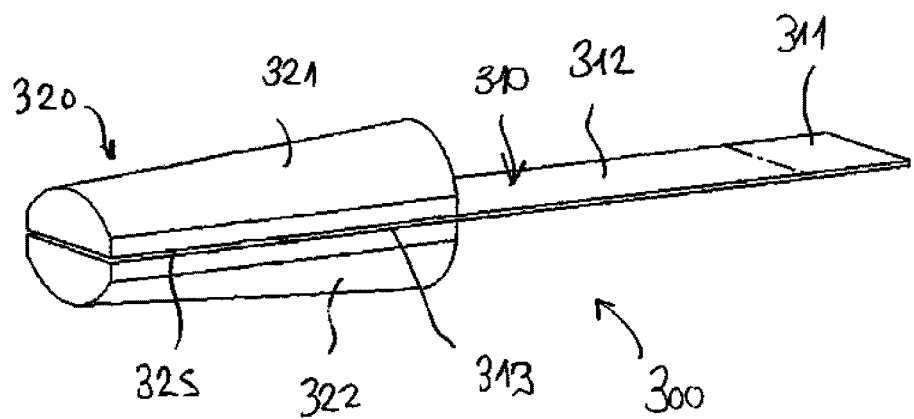
FIG. 3 is a perspective view of one of an energy-generating element of the capsule shown in FIGS. 1 and 2.
Figure 3A:
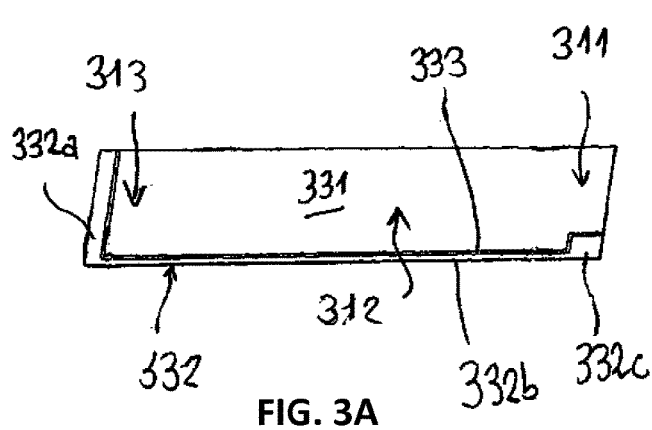
FIGS. 3A and 3B are perspective views of the piezoelectric blade of the energy generating element presented in FIG. 3, according to two different orientations.
Figure 3B:
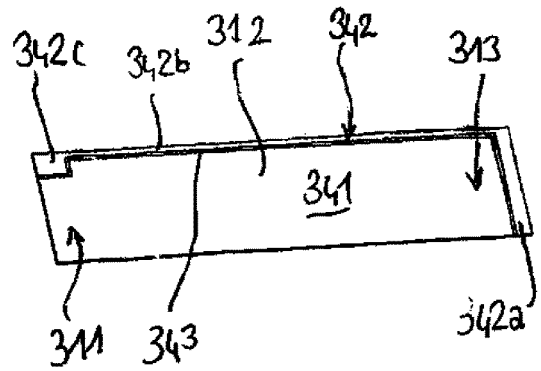
Figure 4:
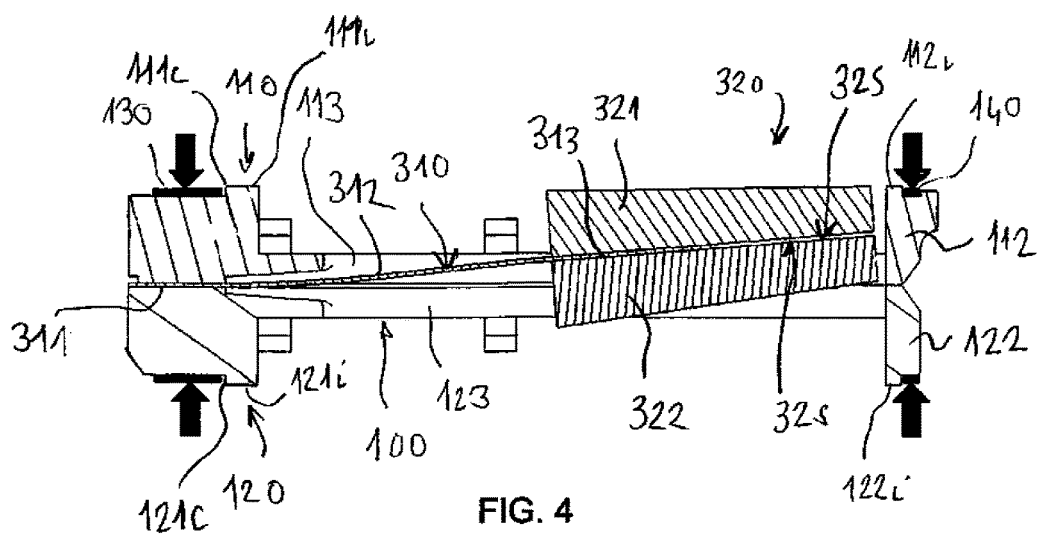
FIG. 4 is an axial section view of a frame pertaining to the capsule and the energy-generating component.
Figure 5:
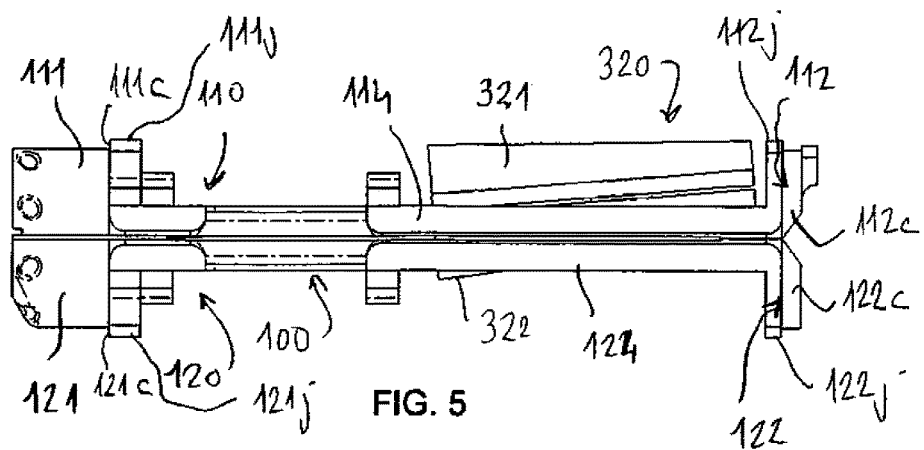
FIG. 5 is a view in side elevation of a capsule frame and the energy-generating element.

FIGS. 3A and 3B show the configuration of a set of metallization provided on the piezoelectric blade.

The blade 310 has on each one of its sides, upper side, see FIG. 3A; lower side, see FIG. 3B, two metallizations 331, 332 and 341, 342, respectively, respectively dedicated to the function of generating electrical energy and to the accelerometric function.

Metallizations 331, 341 dedicated to the feature of generating electrical energy are made of two pads essentially rectangular extending from the terminal edge at the level of the embedding region 311 up to the vicinity of the opposite terminal edge at the level of area 313.

Metallizations 332, 342 dedicated to the accelerometric feature have a configuration that is essentially in an L-shape, with an area 332a, 342a respectively, also called capture area, extending along the terminal edge at the level of area 312, and an area 332b, 342b respectively, extending along a longitudinal edge of the blade 310 to reach a connection pad 332c, 342c respectively, located at the level of the embedding region 311.

In this way, the connections with the electronic unit 200, both to collect the electrical energy generated as supply as well as transmitting the accelerometric signals, are advantageously reported at the level of the embedding region 311, and wired connections can be set-up in this area for this purpose, the frame sections 111, 121 receiving this embedding region 311 being arranged accordingly.

The metalized zones 331, 332 and 341, 342 respectively are electrically insulated from each other by a narrow non-metalized strip 333 and 334 respectively.

Figure 6:
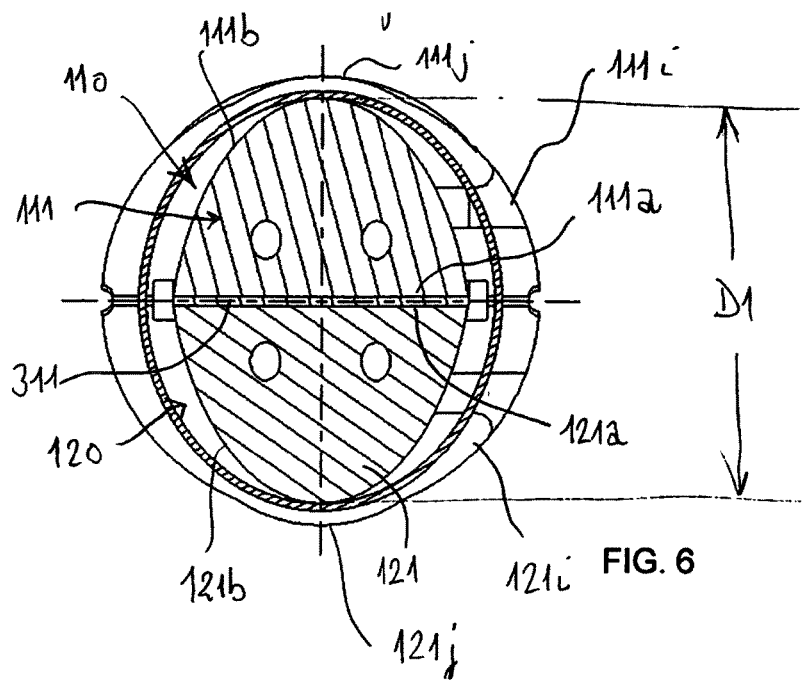
FIG. 6 is a cross-section view of a region where the energy-generating element is embedded into the frame.

As can be seen in FIG. 6, end sections 111, 121 define, when placed opposite each other, two flat sides, 111a, 121a respectively, whose widths are substantially the same as the width of the piezoelectric blade 310, in particular in the blade's embedding section 311, and a dome-like side, 111b, 121b respectively, generally shaped as a semi-ellipse. The blade's embedding section 311 is intended to be placed between the sides 111a, 121a, the cumulative dimension, in radial direction, of the blade and of sections 111, 121 that encompass it being denoted D1.

The embedding section 311 of the blade 310 is placed between the sections 111, 121 of the elements 110, 120, these sections being subjected to radial forces directed towards each other due to an elastically deformable ring 130 placed around the sections 111, 121. It is observed that the sections 111, 121 of the frame elements 110, 120 are those that are the closest to the end 2 of the implant, that is to say the opposite end to the anchoring end 3 anchored to the heart wall, which allows for better signals, both for acceleration and energy recovery, compared to the reverse situation (not shown).

This ring 130 is, for example, manufactured by machining, laser cutting, electrical discharge, or any other method for shaping metallic components. It is made out, for example, of stainless steel, of a nickel-cobalt-type alloy such as MP35, of a titanium alloy, etc.

As a variation, the ring may be made out of a synthetic material such as a Tecothane or Pellethane type thermoplastic polyurethane (registered trademarks), a PEEK (polyether ether ketone), etc.

The ring 130 has a circular profile and is dimensioned so that his inner diameter at rest is less than the abovementioned distance D1. In this way, when the ring 130 is put in place by elastic deformation (as will be described later on), its tendency to regain its shape at rest exerts forces, directed towards each other, on the summits of the dome-like sides 111b, 121b of the sections 111, 121.

More specifically, the elastic deformability of the ring 130 allows making it take on an oval shape by subjecting it to a lateral pressure during the assembly operation, until reaching an inner dimension, vertical on FIG. 6, greater than the dimension D1. Once the ring is released, it exerts the abovementioned forces in order to firmly retain the piezoelectric blade's embedding section 311 between the sections 111, 121. Here, it is important to stress that an axially inner shoulder, 111c, 121c respectively, is provided on the sections 111, 121 in order to allow the correct positioning of the ring 130 during assembly operations.

Depending on the desired retention force and on the manufacturing and assembly constraints, the skilled person will know how to select the material, thickness and inner diameter of the ring 130.

It is understood that the desired effect can be obtained with different geometries for the sections, 111, 121 and the ring 130.

Advantageously, and especially in order to avoid a possible opening between the elements 110 and 120 of the frame at the opposite end of the ring 130, another ring 140 made according to the same specifications as for the ring 130 clamps around the end sections 112, 122 of elements 110, 120 of the frame 100. Here, the clamping force may be lower, given that there is no energy generator 300 embedding function. Therefore, the ring 140 is not as wide as the ring 130, which allows limiting the axial congestion of sections 112, 122. As is observed in particular in FIGS. 4 and 5, this ring 140 is retained in a groove 112c, 122c, defined by the sections 112, 122.

The elongated frame 100 made out of components 110 and 120 is dimensioned so that it closely fits in the tubular casing of the implant, while playing a positioning and fixing role for its whole set of technical features, e.g. electronic circuits, electrical conductors, energy generator. The piezoelectric generator 300 accommodated in the interval between the lateral arms 113, 123 and 114, 124.

Figure 7:
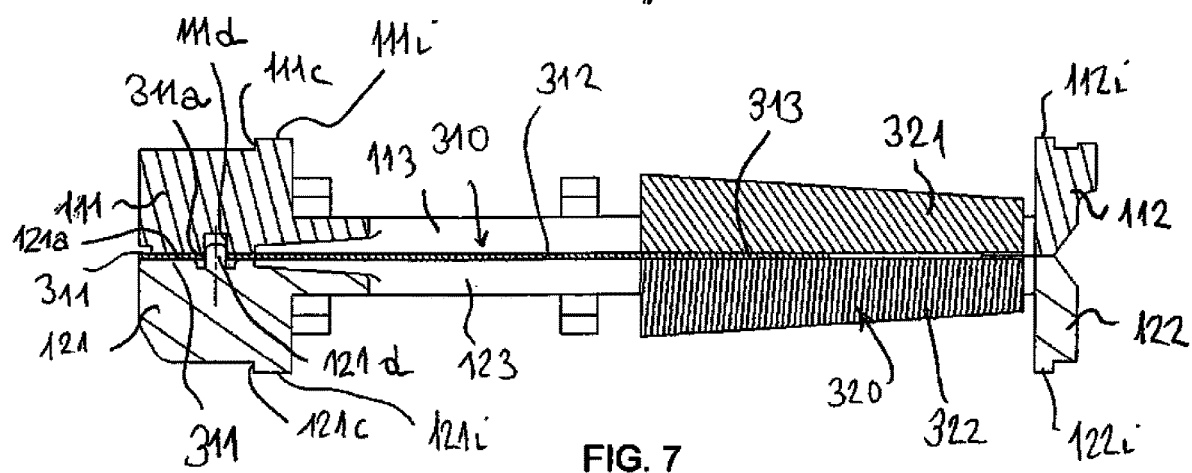
FIG. 7 is an axial section view similar to FIG. 4, showing an alternative embodiment of the embedding.
Figure 8:
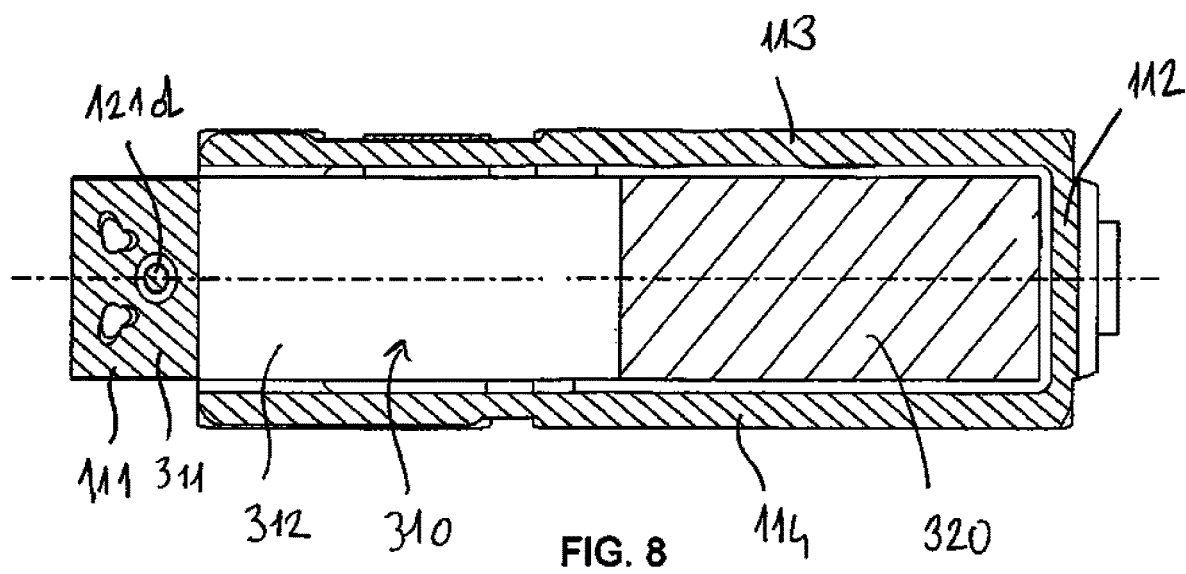
FIG. 8 is an axial section view, at 90° of the one in FIG. 7.

Referring now to FIGS. 7 and 8, an arrangement for stabilizing the position of the blade 310 will be described, in particular in the presence of shock during transportation of the implant (the constraints being defined in the EN45502 standard). In order to avoid accidental shifting of the blade during such shocks, displacements which are possible despite the clamped embedding, a cylindrical pin 121d is formed in section 121, projecting upwardly from its flat side 121a. Similarly to this pin, the embedding region 311 of the blade 310 has a through opening 311a in which the pin, during assembly, fits with minimal or no clearance. Opposite the pin 121d, the opposite flat side 111a has a complementary recess 111d.

In this way, when a shock is applied in the longitudinal axis of the system, the pin 121d opposes itself to the mechanical shear force generated mostly by the inertia of the masses 321, 322. The diameter of the pin is, for example of about 1 to 3 mm, depending on the level of the shearing force to be neutralized.

The shape of the pin 121d can, of course, vary and several pins can be foreseen.

FIG. 8 gives an estimation of the clearance provided between the energy generator 300 and the frame structure that surrounds it. This clearance allows allowing the freedom of movement of the blade 310 with the masses 321, 322 during its vibrations. It is selected according to the dimensional accuracy of manufacture of the frame and the generator and of their mutual assembly, and is, for example, 0.1 mm.

Figure 8A:
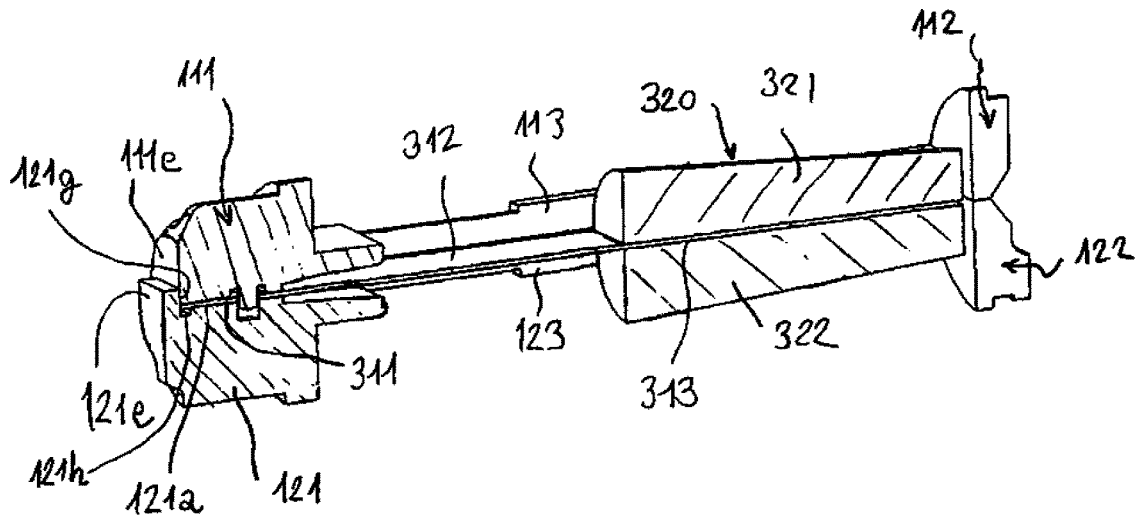
FIG. 8A is a partial axial section view of another embodiment of the embedding.

Referring now to FIG. 8A, the stabilization of the position of the blade in translation in the longitudinal direction of the implant, and in rotation about an axis perpendicular to the plane of the blade can be improved by clamping the free edge of the embedding region 31. More specifically, section 121 of the frame component 120 has here an axial dimension slightly larger than that of section 111, with a wall 121e coming into contact with the free edge of the blade's embedding region 311 as well as with the free axial end side 111e of the section 111. It is to be noted that in FIG. 8A, the pin is provided on component 111 and not on component 121; the resulting effect, however, being the same.

Furthermore, in order to prevent the rear edge of the blade from leaning imperfectly against the curvature, which could occur during the manufacturing of frame components by plastic material injections, connecting the side 121a with the internal side 121g of the wall 121e, a small recess 121h is provided at the foot of the wall. This recess can, for example, have a depth and a width of a fraction of a millimeter. This way, one prevents that the connection between the embedding region 311 of the blade and the frame becomes hyperstatic.

The frame is placed into the tubular casing 10, narrowly and without clearance, due to its greater transversal section regions. These regions are, here, zones 111i, 121i, 112i, 122i belonging to the respective end sections 111, 121 et 112, 122 of the frame components, innerly adjacent to the areas receiving the rings 130, 140 respectively, these areas having a generally circular cross section whose diameter corresponds to the inner diameter of the tubular casing 10, this section appearing, however, as a set of pads, 111j, 121j, 112j, 122j respectively, here diametrically opposed in pairs, giving locally to these areas a diameter slightly larger than the inner diameter of the casing, for example in the order of 0.05 to 0.1 mm. In this way, one creates a negative clearance in order to compensate for any potential defects of geometry by ensuring the immobilization of the frame 100 mounted inside the casing 10. It can be optionally provided a bond between the frame and the casing in order to completely remove the risk of displacement.

Figure 9:
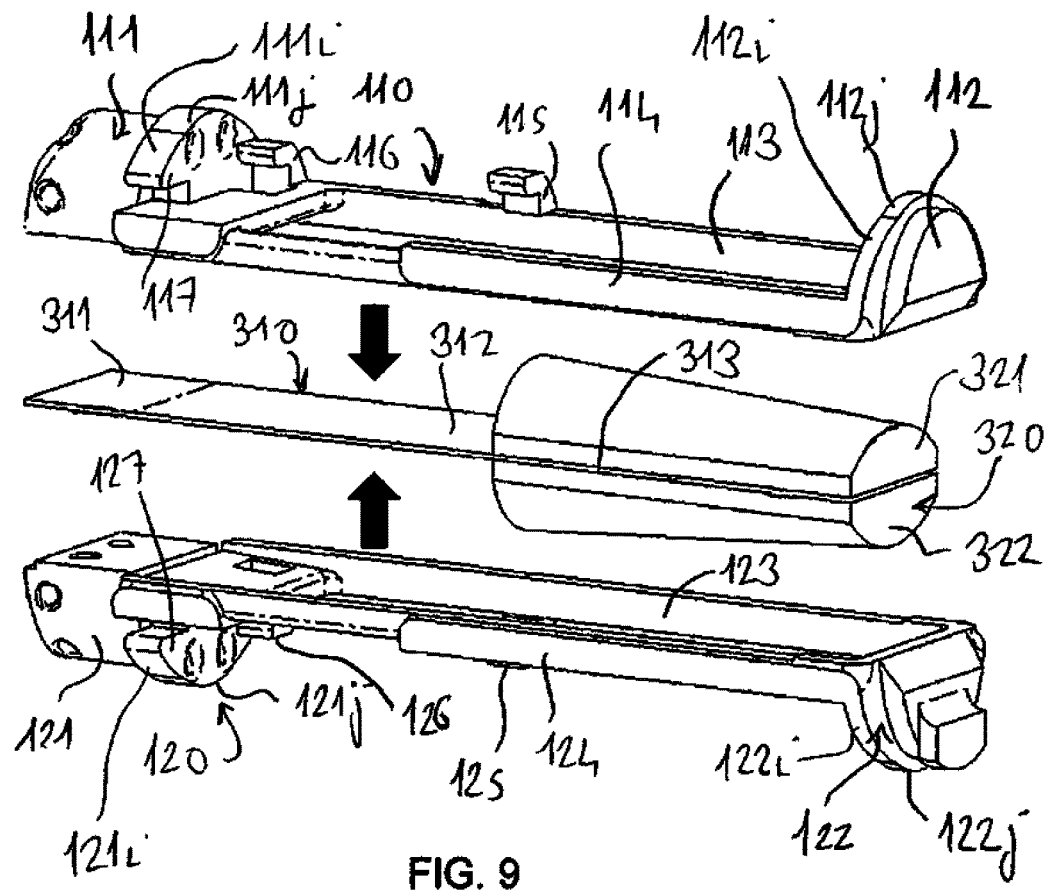
FIGS. 9 and 10 are two fragmented perspectives showing two main steps in the assembly of the inner components of the capsule described in FIGS. 1 to 6.
Figure 10:
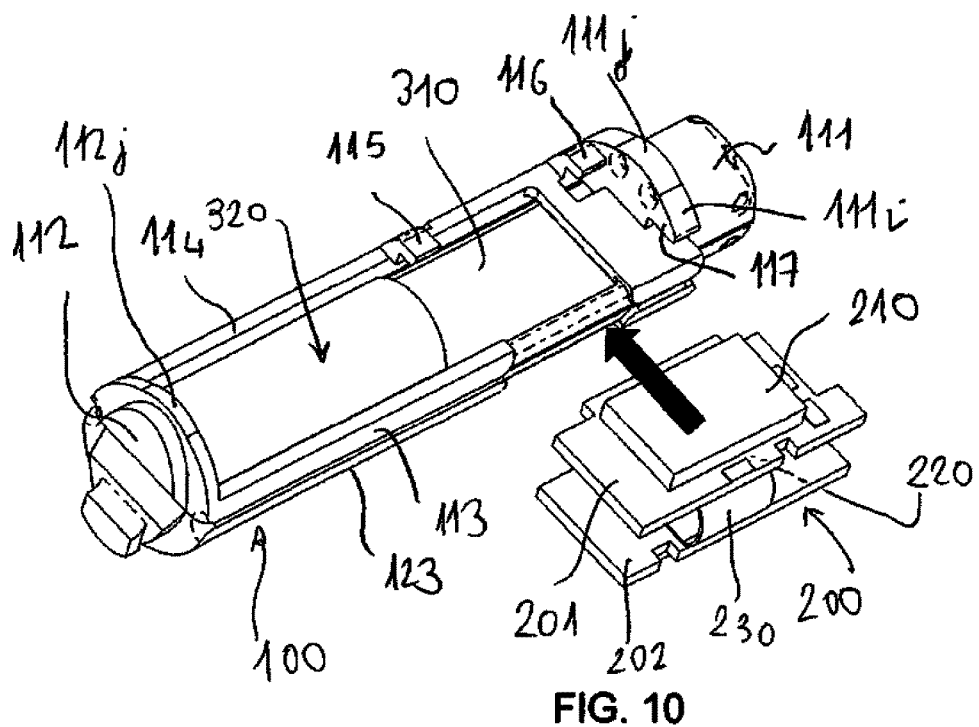

Referring in particular to FIGS. 9 and 10, the layout and assembly of the various elements will now be described, excluding the embedding of the blade 310, previously described, to the frame 100.

First, in order to further improve the use of the space inside the implant, the installed electronics 200 is in the form of two electronic circuits 210, 220, preferably integrated circuits rather than discrete components, attached respectively to two miniature printed circuit boards 201, 202, the circuits being connected together by a flexible sheet of conductors 230. In FIG. 10, the circuit 220 is not visible. These elements are housed on one section of the frame, leaving the necessary space and situated over the free region 312 of the piezoelectric blade 310.

The configuration of each board 201, 202 is such that it can be engaged under a set of clamps, 115, 116, 117 and 125, 126, 127 respectively, formed on the frame elements 110, 120. More specifically, two clamps 115, 116 are formed projecting upwardly from the arm 114 of the frame element, essentially at the level of the blade's free region 312, whereas the clamp 117 is formed by a recess included in section 111i of the frame element 110. The board 201 can thus be inserted by translation below these clamps. The electronic unit 200 is such that it can be laterally mounted on the frame 100 by leaving between the boards 210, 220 the space required by the movement of the central section of the piezoelectric blade 310. Restraining the boards 210, 220 onto the frame 100 is achieved by gluing and/or clipping, for example.

On the opposite side, the side of the frame element 120, the printed circuit board 202 is mounted according to the same principle.

In this way, the electronic unit 200 is set up by translation in a radial direction, as shown by the arrow in FIG. 10, each board lodging itself under these respective clamps, as described, and the flexible sheet 230 being placed laterally in a matching recess 113a foreseen in the lateral arm 113.

The restraint of the board is guaranteed, for example, by foreseeing a negative clearance between the space defined by the clamps and the thickness of the respective board. Glue can be used to strengthen the restraint.

It is to be noted that the FIGS. 9 and 10 differ from each other, one being the mirror image of the other.

Regarding FIG. 11, the arrangement of the various electrical and electronic elements of the implant on the frame will be described. In some embodiments, the upper printed circuit board 201, with respect to the orientation of the figures, has most of the connecting pads with different organs. The lower board 202 has two connecting pads for the connection, by two respective flexible cables, with metallization formed on the lower side of the piezoelectric blade 310.

Figure 11:
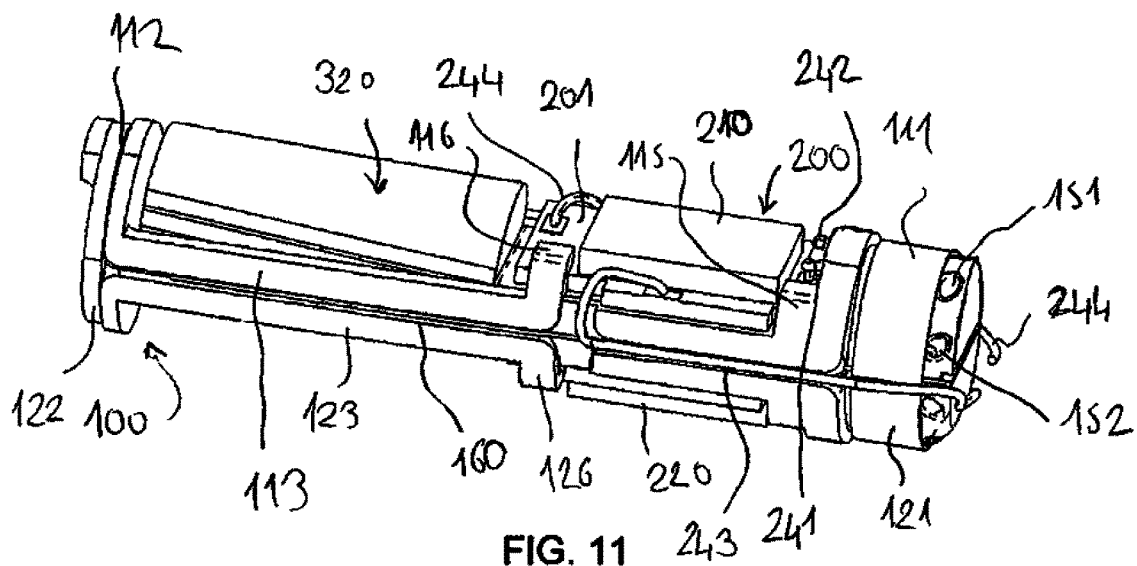
FIG. 11 is another perspective view of the capsule's inner architecture.

Shown in FIG. 11 are two flexible conductors 241, 242, which connect the upper board 201 with metallization formed on the upper side of the piezoelectric blade 310, passing through two holes drilled in said board.

References 151, 152 represent holes made in section 111 of the upper frame element 110 to inject conductive glue to connect the conductors 241, 242 with their respective metallization located on the upper side of the blade 310. Other non-visible holes are formed for the same purpose in section 121 of the lower frame element 120.

Flexible conductors 243, 244 make the connection of the upper printed circuit board 201 with a battery, not shown, whose charge is meant to be secured or maintained by the electrical generating unit 300.

Moreover, the arms 113, 123 together define a groove 160, for a flexible conductor, not shown, connecting the implant's front electrode, not shown, to the upper board 201. Although not visible, the arms 114 and 124 define a similar groove.

Figure 11A:
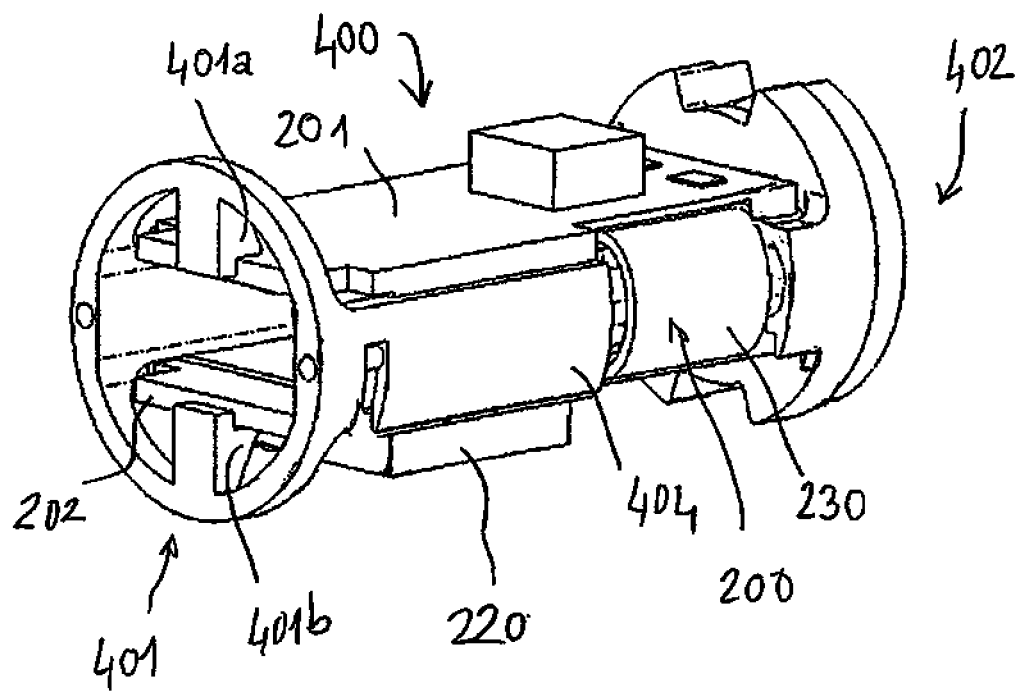
FIG. 11A is a partial perspective view of an alternative embodiment of a frame, to receive an electronic unit.
Figure 11B:
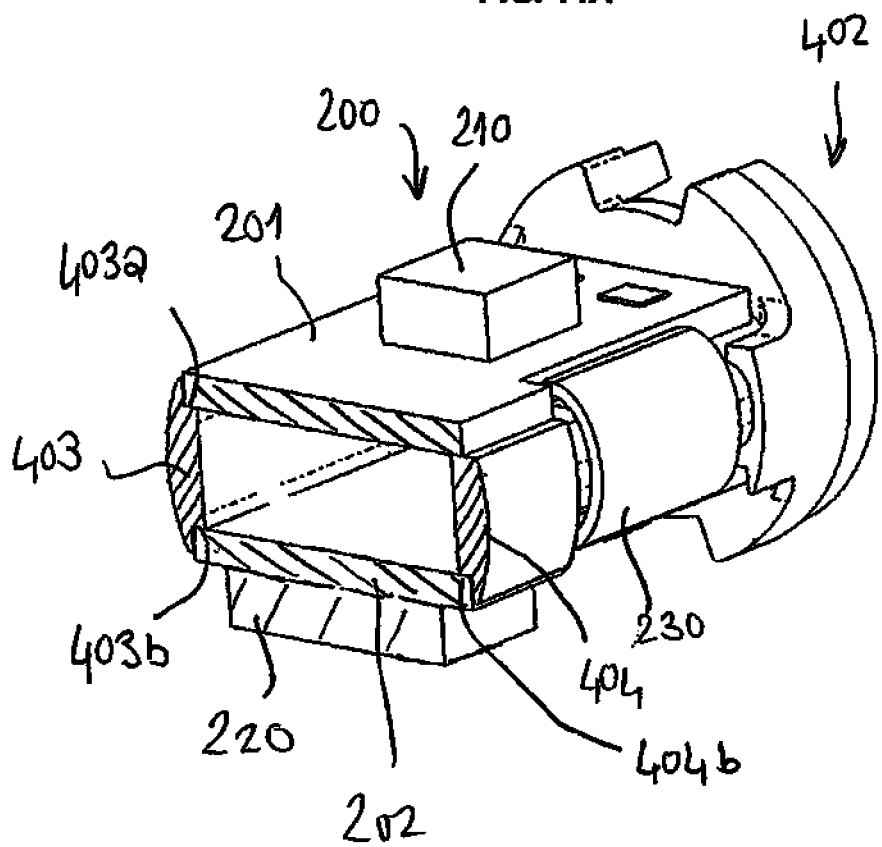
FIG. 11B is a partial view of FIG. 11A, offering both a perspective and a cross-section view thereof.

FIGS. 11A and 11B illustrate an alternative embodiment to simplify the assembly of the electronic unit 200 and to increase the space available for this unit. To this end, the frame 100 is made of two axial sections, only the section 400 forming a support to the electronic unit 200 is represented, while the other section, designed for the embedding of section 311 of the blade 310 is not shown.

This section of the frame 400 is, for example, made up of synthetic material and comprises two end sections 401, 402 which have a transversal section adjusted on the inside area of the implant's casing 10, and two lateral arms respectively 403, 404, equipped with adjustments to restrain the printed circuit boards 201, 202.

Elastic retention teeth respectively 401*a*, 401*b*, are provided at the level of the end section 401, each tooth ensuring the retention of the respective printed circuit board in a radial direction. Moreover, the board 202 is supported in, its plane and perpendicularly thereto against two shoulders 403*b*, 404*b* respectively formed along the lower edges of the arms 403, 404, while the board 201, leans against a shoulder 403*a* formed along the length of the upper edge of the arm 403. Regarding the arm 404, there is no lateral shoulder function for the board 201 so as to allow the positioning of the latter by a movement of rotation about the central axis of the sheet of conductors 230.

The final immobilization is achieved, for example, by binding section 402 and the adjacent edges of the boards 201, 202. Alternatively, the boards 201, 202 can also be restrained with retention teeth at the level of this section 402.

Figure 12:
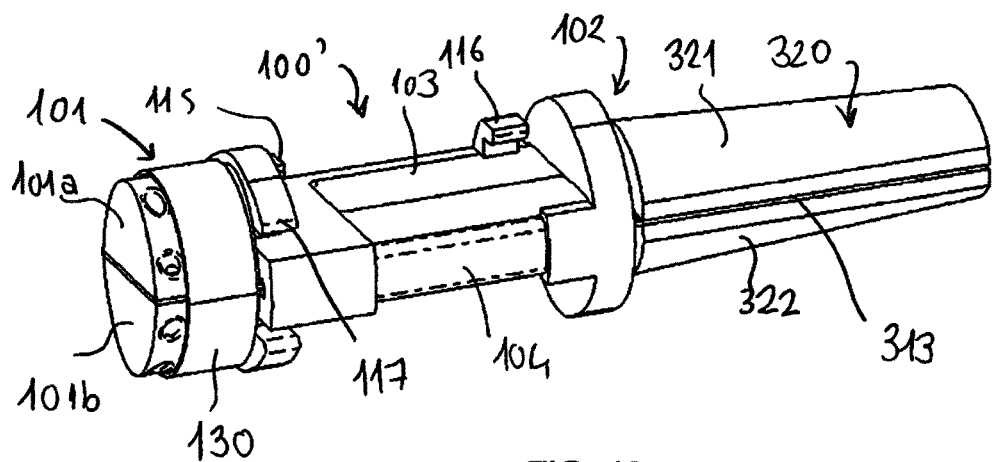
FIG. 12 is a perspective view of a frame and of an energy-generating element according to a second embodiment.
Figure 13:
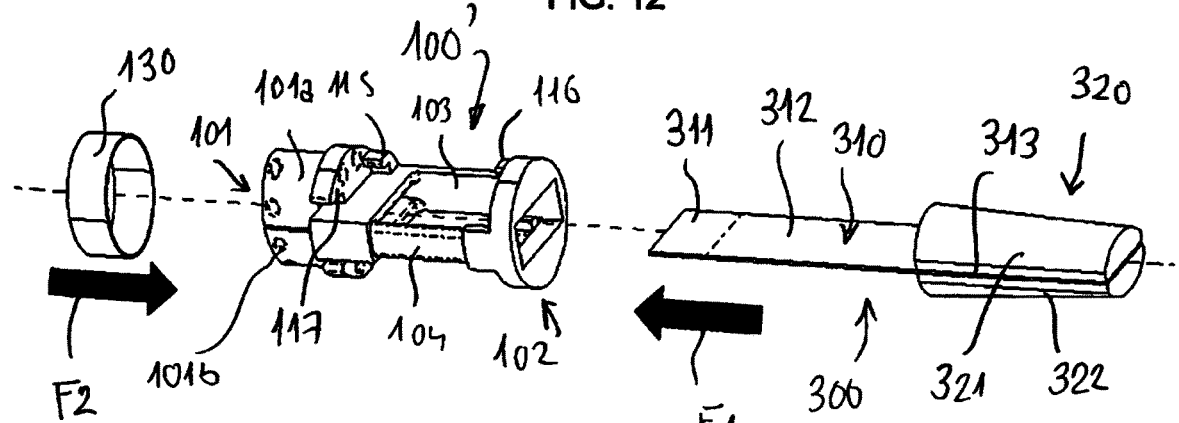
FIG. 13 is a fragmented perspective of the elements of FIG. 12, illustrating the assembly phase.
Figure 14:
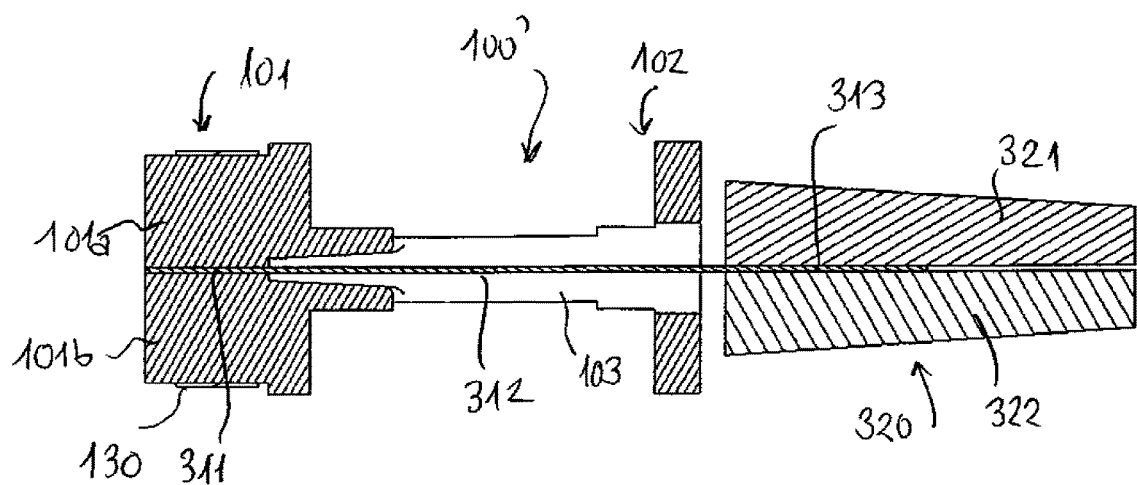
FIG. 14 provides an axial section view of the elements of FIGS. 12 and 13.

We shall now describe—regarding FIGS. 12 to 14—an alternative embodiment of the disclosure where the frame 100 receiving the energy generator 300 is made of one single piece and where the frame's support inside the tubular casing 10 is achieved not in the sections of the two axial ends of the implant, but in the section 101 of an axial end, on the embedding side of the generator 300, also called first support section, and in an axially intermediate section 102, also called second support section, the inertial mass 320 of the generator extending in cantilever with respect to the frame 100'.

Lateral arms 103, 104 reunite these sections. The region 101 is made up of two sections 101*a*, 101*b*, slightly movable with respect to each other, e.g. because of the deformability of the material of the frame, and delimiting between them a free space having a thickness essentially equal to the thickness of the blade 310 in its embedding region 311. As in the previous embodiment, a ring 130 placed around the sections 101*a*, 101*b* allows to grip the aforementioned region 311 with the required force.

Here it is important to note that this frame 100' has similar arrangements to those of the frame 100 for receiving both the electronics and the connections.

This variation allows a cost reduction for the tooling and for the number of parts to be manufactured.

The mounting of the generator is done by axial translation of the latter in the direction of the arrow F1 in FIG. 13, the ring 130 being then moved according to the arrow F2.

Because of the cantilevered mounting of the inertial mass, its size must be determined in a way to provide, in relation to the implant's casing 10, a sufficient clearance to allow for support of the frame on the casing at one end only and in an axially intermediate region.

Now with reference to FIGS. 15 to 17, another alternative embodiment will be described where the embedding of the piezoelectric blade is achieved without the implementation of any specific clamping force.

In this embodiment, the embedding region 311 of the blade prior to being assembled, receives an overmolding 330. The overmolding 330 of region 311 of the blade 310 can incorporate one or more rigid components, either in contact with the blade 310, or submerged in the overmolding. These elements serve to increase the rigidity of the overmolded unit, for example, by adding metallic components such as stainless steel spacers.

The frame 100", once again composed of one single piece, has two blocking sections in the implant's tubular casing 10, located this time, in the implant's axial end sections, and here again, has, at the level of its lateral arms 103, 104, means for receiving and fixing the electronics 200.

Figure 16:
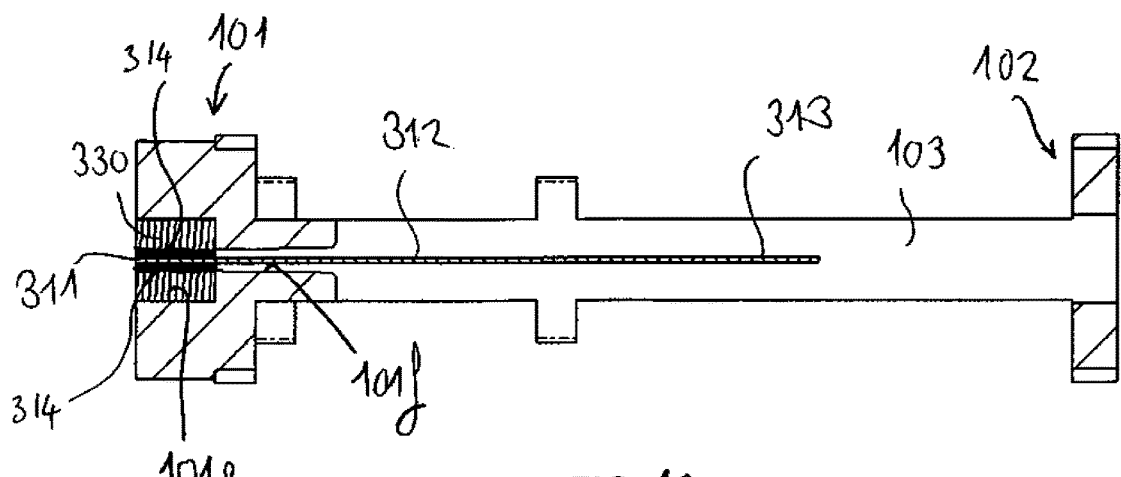
FIG. 16 is an axial section view of the energy-generating element and of the frame of FIG. 15 after assembly.
Figure 17:
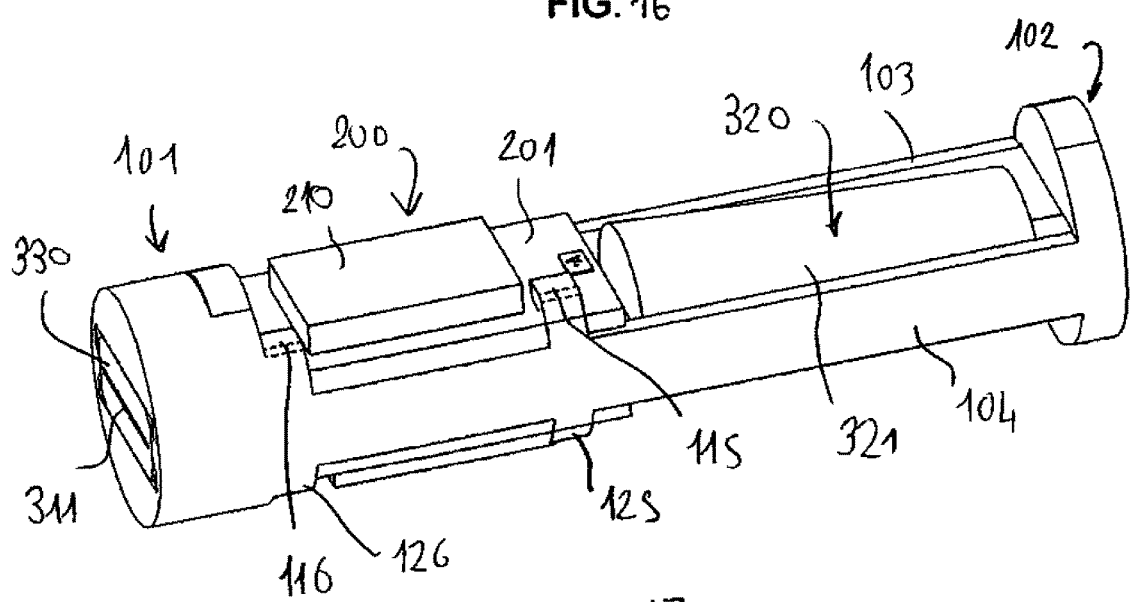
FIG. 17 offers a perspective view of the energy-generating element and of the frame of FIGS. 15 and 16 as well as of the electronic unit.

Section 101 of the frame has a recess 101*e* whose shape is generally complementary to the shape of the overmolding 330 and extends itself to a throughout passage 101*f*, whose cross section is substantially greater than that of the blade 310, so as to allow its displacement during oscillations, as shown by FIG. 16.

Figure 15:
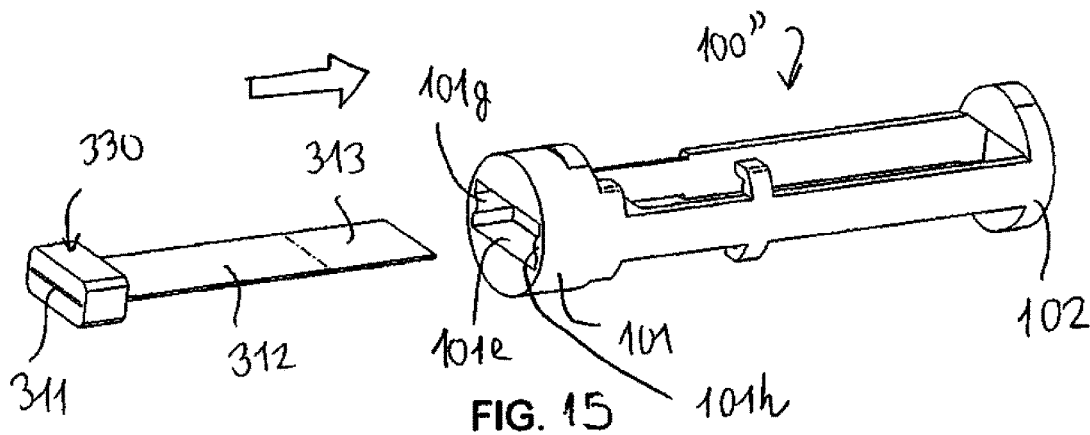
FIG. 15 is a fragmented perspective view of an energy-generating element and a frame according to a third embodiment.

The assembly is performed by engaging the blade 310, without the elements 321, 322 forming the inertial mass, in the direction of the arrow in FIG. 15, so that the overmolding slides neatly into position and is blocked in its recess 101*e*. This blockage is advantageously carried out thanks to two lateral pads 101*g*, 101*h*, provided in the recess 101*e* and creating, together with the overmolding 330, a negative clearance. The final binding can be done by gluing.

Only then are the inertial mass elements 321, 322 added to the region 313 of the blade and fixed, for example as described previously.

This variant avoids subjecting the sides of the blade to clamping forces. Indeed, the forces resulting from the embedding action have little to no impact on said sides.

Figure 18:
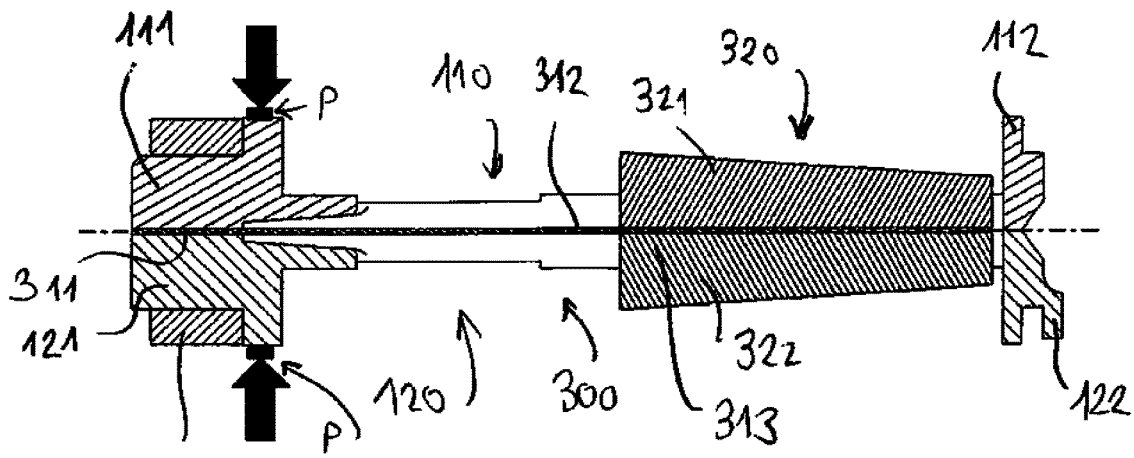
FIG. 18 is an axial section view of a frame according to an alternative embodiment of the implant of FIGS. 1 to 6, the energy-generating element being also represented.
Figure 19:
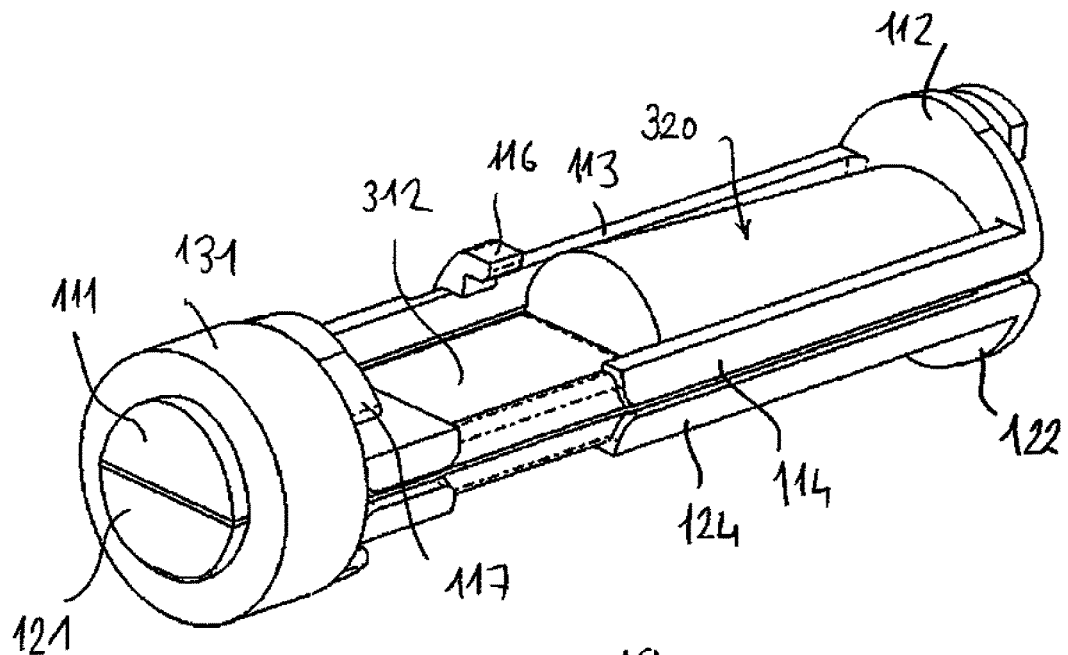
FIG. 19 is a perspective view of the ensemble of FIG. 18.
Figure 20:
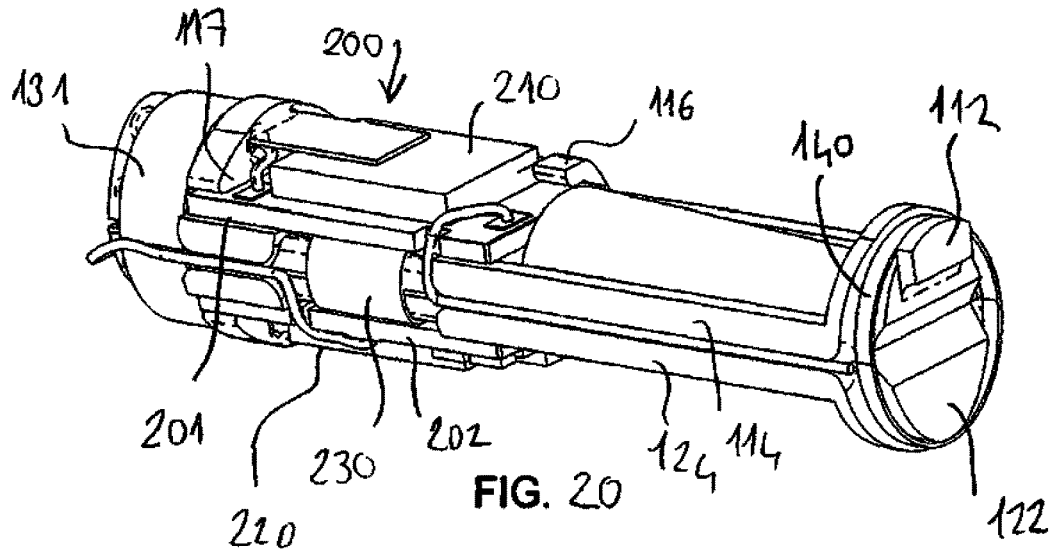
FIG. 20 is a perspective view from another angle of the set of FIGS. 18 and 19, and the electronic circuits and conductors assembled on this unit.

FIG. 18 shows a variation of the first embodiment of the disclosure, where again, the embedding region 311 of the piezoelectric blade is clamped between two sections 111, 121 of the frame by a clamping force. However, in this case, the clamping of sections 101*a*, 101*b* is achieved by using a specific tool, such as a P clamp, illustrated by arrows and letter P, and while the clamped position is being held, a ring 131 is overmolded around sections 112, 121 onto the frame in order to ensure the final retention of the blade 310, after which, the force exerted by the P clamp can be removed, as shown in FIGS. 19 and 20.

Figure 20A:
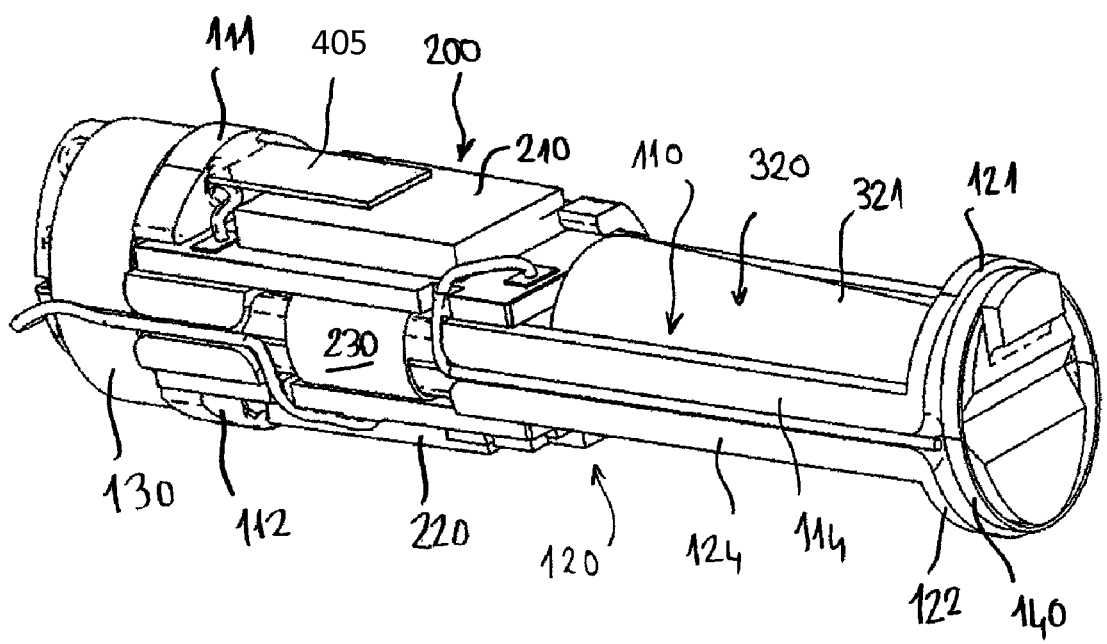
FIG. 20A is a perspective view of an implantable capsule according to another embodiment.

Referring now to FIG. 20A, another embodiment is shown, wherein the accelerometry and the energy-generating features are achieved by two different piezoelectric blades. In this figure, the axis of perspective is reversed compared to the one in FIG. 2, identical or similar elements or sections are designated by the same references and will not be described again.

The energy-generating feature is provided by a unit 300 generally identical to the one described in the first embodiment, except, however, for the metallization, which are simplified due to the fact that the accelerometry feature is in this case absent.

In this case, the accelerometry feature is performed by a dedicated piezoelectric blade 405, with substantially smaller dimensions, which is also embedded into the area of the frame made up of sections 111, 112, joined by the ring 130, in a plane located away from the plane occupied by the blade 310 at rest. The piezoelectric blade 405 can be devoid of inertial mass and has two metallizations on its respective sides, connected to the electronic unit 200 by flexible wires.

Regarding the accelerometry feature, a deformation of a few micrometers generating a differential voltage with variations of the order of nanovolt is generally sufficient for a signal post-processing by the electronic unit 200. The piezoelectric blade 405, therefore, may be significantly smaller than the piezoelectric blade 310, for example, with dimensions of the order of 1 mm×3 mm.

In this manner, an accelerometer is realized on one dimension of the space, (the axis perpendicular to the plane of the blade 405,) sufficient to capture the heart's kinematics. It is, of course, possible to add one or two piezoelectric blades oriented differently from the blade 405, in order to make the accelerometer multidimensional.

Alternatively, it is also possible to provide an acceleration feature along an axis through the unit 300, and an acceleration feature according to one or two other axes with additional blades of the 405 blade-type, orientated in a non-parallel fashion to the blade 310.

Figures 21A, 21B:
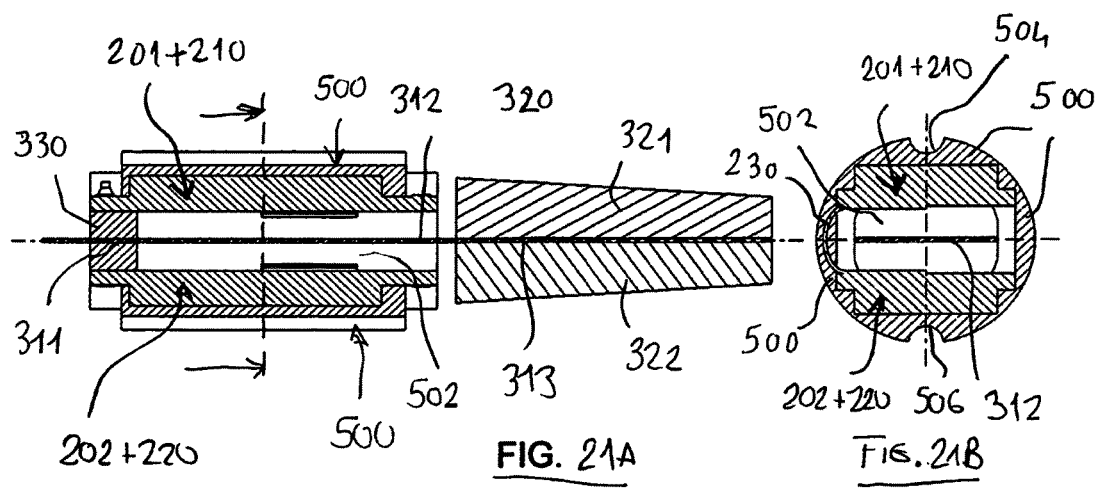
FIG. 21A is an axial section view of a frame/energy generator/electronic circuits unit, according to a fourth embodiment of the disclosure.
FIG. 21B is a cross-section view along the dash line of FIG. 21A.
Figure 22:
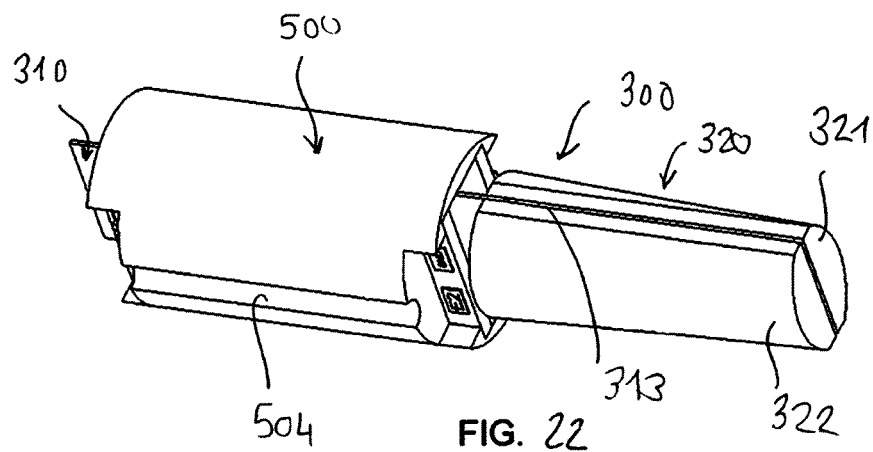
FIG. 22 is a perspective view of the set of FIGS. 21A and 21B.

Now, referring to FIGS. 21A, 21B and 22, another embodiment will be described where the embedding of region 311 of the blade 310 and the retention of the piezoelectric electronic unit 200 are carried out in a single joint molding operation.

Thus in this embodiment, there is no specific frame, nor any mounting of the energy generating element 300 and of the electronic circuits on such a frame. The overmolded section is designated by reference number 500 and acts as a frame after the overmolding operation. The mold and its various components are designed so as to confer to the overmolded section a generally cylindrical external surface adjusting itself to the implant's tubular casing, a central passage 502 dimensioned so as to allow the free oscillations of the electrical energy generator 300 and diametrically opposed longitudinal grooves 504, 506 for the passage of flexible conductors. As shown, the embedding section 311 of the blade 310 is first previously equipped with an overmolding 330, as in the embodiment of FIGS. 15 to 18.

The mold is of course positioned so as to maintain the elements to be molded in place: primarily the generator 300 and the electronic circuits 200.

In this variation, the embedding is formed solely by molding. This implies a more complex industrialization procedure than the previous variations, but offers a better reliability and repeatability of the components' assembly.

There is an industrial advantage, as this solution does not have any main unit supporting the components, which implies lower manufacturing costs, e.g. fewer pieces to assemble, fewer molds.

Of course, the present disclosure may be subject to numerous variations and modifications. In particular, it can be implemented in any implant requiring a source of electric energy for supplying electrical or electronic circuits. The energy generator 300 is therefore configured and dimensioned according to the needs in terms of energy, available space and potential weight constraints. Advantageously, the distance between the embedding point and the center of gravity of the inertial mass 320 is determined in such a way as to generate beats according to a natural frequency of the mobile unit.

Furthermore, one or more features of the various embodiments illustrated can be combined individually or in groups with one or more features of at least one other embodiment.

What is claimed is:

1. An implantable autonomous heart stimulation capsule, comprising:
    an elongated tubular body structured to pass through a portion of a vasculature and having:
        at a first end, a releasable linking device connectable to an installation lead; and
        at a second end, a surface having a spiral anchoring element for anchoring the implantable autonomous heart stimulation capsule to a heart wall, wherein the spiral anchoring element extends helically about a central axis and away from the surface, and the elongated tubular body housing a frame supporting an electronic unit; and
    an accelerometer, wherein the accelerometer comprises:
        a piezoelectric blade extending cantilevered from an end region of the piezoelectric blade embedded into the frame and in a direction from the first end to the second end, wherein the piezoelectric blade extends cantilevered in a direction substantially parallel to the central axis of the spiral anchoring element, and the piezoelectric blade extends cantilevered in a direction substantially perpendicular to the surface.

2. The implantable autonomous heart stimulation capsule according to claim 1, wherein the piezoelectric blade forms an electrical energy generator to supply the electronic unit.

3. The implantable autonomous heart stimulation capsule according to claim 1, further comprising an inertial mass attached to the piezoelectric blade in an area away from the embedding region.

4. The implantable autonomous heart stimulation capsule according to claim 3, wherein the inertial mass has dimensions which decrease when moving away from the piezoelectric blade's embedding region.

5. The implantable autonomous heart stimulation capsule according to claim 3, wherein the inertial mass comprises two identical elements attached each on one side of the piezoelectric blade.

6. The implantable autonomous heart stimulation capsule according to claim 5, wherein the two identical elements are attached each on one side of the piezoelectric blade in a free end region thereof.

7. The implantable autonomous heart stimulation capsule according to claim 1, wherein the piezoelectric blade comprises on each one of its sides a first metallization for collecting an acceleration signal and a second metallization for collecting electrical energy.

8. The implantable autonomous heart stimulation capsule according to claim 7, wherein the first metallizations each comprise a capture area situated in the blade's end region opposite to the embedding region of the piezoelectric blade.

9. The implantable autonomous heart stimulation capsule according to claim 8, wherein the first metallization comprises an area extending along an edge of the blade between the capture area and the embedding region of the piezoelectric blade.

10. The implantable autonomous heart stimulation capsule according to claim 1, wherein the frame comprises two frame elements assembled together and wherein the piezoelectric blade's embedding region is clamped between two opposing sections of the two frame elements.

11. The implantable autonomous heart stimulation capsule according to claim 10, wherein the two frame elements are assembled together in a radial direction.

12. The implantable autonomous heart stimulation capsule according to claim 10, wherein the two opposing sections of the two frame elements are end sections.

13. The implantable autonomous heart stimulation capsule according to claim 10, comprising at a level of said opposing sections, a clamping ring holding said opposing sections of the two frame elements.

14. The implantable autonomous heart stimulation capsule according to claim 1, wherein the piezoelectric blade's embedding region is located in near the first end of the implant.

15. The implantable autonomous heart stimulation capsule according to claim 1, further comprising a second piezoelectric blade functioning as a generator for collecting electrical energy to supply the electronic unit.

16. The implantable autonomous heart stimulation capsule according to claim 15, wherein the first piezoelectric blade and the second piezoelectric blade are embedded in a same section of the frame.

17. The implantable autonomous heart stimulation capsule according to claim 16, wherein the first piezoelectric blade and the second piezoelectric blade extend in cantilever parallel to one another.

18. The implantable autonomous heart stimulation capsule according to claim 16, wherein the first piezoelectric blade and the second piezoelectric blade extend in the same direction from said frame section.

19. The implantable autonomous heart stimulation capsule according to claim 15, wherein the first piezoelectric blade is smaller than the second piezoelectric blade.

20. The implantable autonomous heart stimulation capsule according to claim 1, wherein the frame is formed by an overmolding.

* * * * *